United States Patent
Hub et al.

(10) Patent No.: US 12,209,066 B2
(45) Date of Patent: Jan. 28, 2025

(54) METHOD FOR CONCENTRATING A WATER-SOLUBLE ORGANIC PEROXIDE

(71) Applicant: ARKEMA FRANCE, Colombes (FR)

(72) Inventors: Serge Hub, Pierre-Benite (FR); Philippe Maj, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 625 days.

(21) Appl. No.: 17/417,445

(22) PCT Filed: Dec. 20, 2019

(86) PCT No.: PCT/FR2019/053265
§ 371 (c)(1),
(2) Date: Jun. 23, 2021

(87) PCT Pub. No.: WO2020/136339
PCT Pub. Date: Jul. 2, 2020

(65) Prior Publication Data
US 2022/0073458 A1    Mar. 10, 2022

(30) Foreign Application Priority Data

Dec. 26, 2018 (FR) ...................... 1874174

(51) Int. Cl.
*C07C 407/00* (2006.01)
*B01D 61/02* (2006.01)

(52) U.S. Cl.
CPC ........ *C07C 407/003* (2013.01); *B01D 61/025* (2013.01); *B01D 2311/02* (2013.01); *B01D 2311/2676* (2013.01)

(58) Field of Classification Search
CPC .................................................. C07C 407/003
See application file for complete search history.

(56) References Cited

U.S. PATENT DOCUMENTS

| | | | |
|---|---|---|---|
| 2,383,919 A | 8/1945 | Rust | |
| 3,945,941 A * | 3/1976 | Borchert | C07C 407/006 252/399 |
| 4,995,983 A | 2/1991 | Eadie et al. | |
| 2004/0220416 A1 | 11/2004 | Emsenhuber et al. | |
| 2012/0024789 A1* | 2/2012 | Sarkar | B01D 69/02 210/500.21 |

FOREIGN PATENT DOCUMENTS

| | | |
|---|---|---|
| EP | 0930269 A1 | 7/1999 |
| GB | 1137717 | 12/1968 |

(Continued)

OTHER PUBLICATIONS

Rusli, Arjulizan, et al, Allylic monomers as reactive plasticizers of ppolyphenylene oxide. Part II: Cure kinetics, European Polymer Journal, Jul. 2, 2011, pp. 1785-1794, vol. 47.

(Continued)

*Primary Examiner* — Medhanit W Bahta
(74) *Attorney, Agent, or Firm* — NK Patent Law

(57) ABSTRACT

The present invention relates to a process for the concentration of a water-soluble organic peroxide, preferably an alkyl hydroperoxide, by reverse osmosis as well as to a process for the separation of a water-soluble organic peroxide and of a water-insoluble compound.

14 Claims, 1 Drawing Sheet

(56) References Cited

FOREIGN PATENT DOCUMENTS

| WO | 2004037782 A1 | 5/2004 |
| WO | 2005054182 A1 | 6/2005 |

OTHER PUBLICATIONS

Ahsan, Laboni et al., "Recovering/concentrating of hemicelluosic sugars and acetic acid by nanofiltration and reverse osmosis from prehydrolysis liquor of kraft based hardwood dissolving pulp process", Bioresource Technology, 2014, pp. 111-115, vol. 155.

Sun, L et al., "Using reverse osmosis to obtain organic matter from surface and ground waters", Pergamon, Water Research, Jun. 1995, pp. 1471-1477, vol. 29, No. 6.

\* cited by examiner

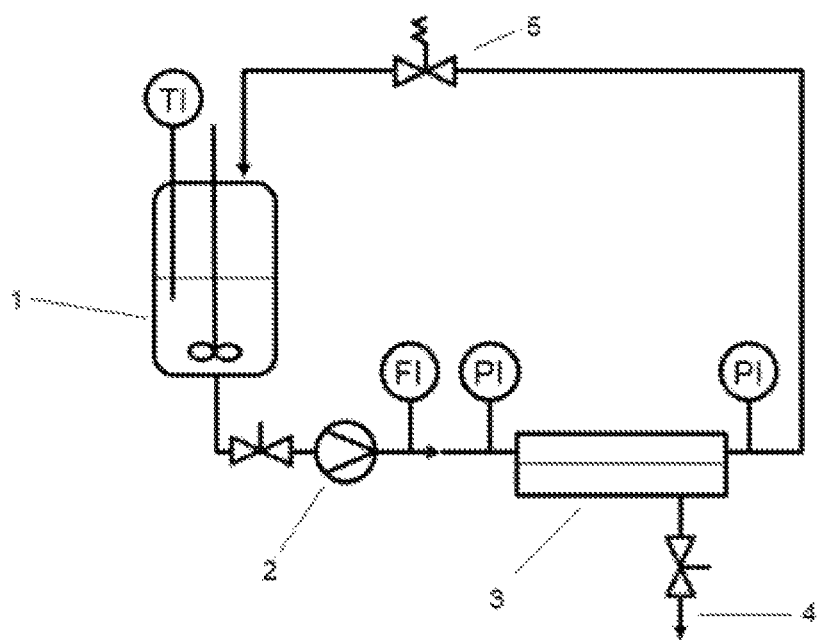

METHOD FOR CONCENTRATING A WATER-SOLUBLE ORGANIC PEROXIDE

CROSS-REFERENCE TO RELATED APPLICATIONS

This application is a U.S. National Stage application of International Patent Application No. PCT/FR2019/053265, filed on Dec. 20, 2019, which claims the benefit of French Patent Application No. 1874174, filed on Dec. 26, 2018.

FIELD OF THE INVENTION

The present invention relates to a process for the concentration of a water-soluble organic peroxide, preferably an alkyl hydroperoxide, by reverse osmosis as well as to a process for the separation of a water-soluble organic peroxide and of a water-insoluble organic peroxide.

TECHNICAL BACKGROUND

The manufacture of hydroperoxides is generally carried out by reaction of the corresponding alcohols or alkenes with hydrogen peroxide using acid catalysts, such as sulfuric acid. They can also be obtained by oxidation of the corresponding alkanes in air or in molecular oxygen. In all of these synthetic processes, undesirable byproducts are formed which must be separated from the desired hydroperoxides.

For example, during the synthesis of hydroperoxides by reaction of alcohols or alkenes with hydrogen peroxide in the presence of sulfuric acid, the acid also catalyzes the formation of symmetrical dialkyl peroxides, the latter representing an undesirable impurity.

In order to be able to separate the undesirable byproducts from the desired hydroperoxides, it is often necessary to carry out several washing operations, resulting in a solution comprising the hydroperoxides in the diluted state. Thus, once this separation stage has been carried out, a reconcentration of the solution comprising the peroxides may be necessary for subsequent applications.

Different methods of concentration of solutions comprising water-soluble organic peroxides, in particular hydroperoxides, are known.

For example, the document WO 2004/037782 describes a concentration process in which the water present in a peroxide formulation is removed using pervaporation technology. The water is removed through a semipermeable membrane. This process requires vaporizing the water. The effectiveness of this technique increases as the organic peroxide solution become hotter, which creates a significant risk in terms of safety. In addition, this process is only suitable for removing small amounts of water.

There thus exists a real need to provide a process making it possible to concentrate a solution comprising a water-soluble organic peroxide, in particular a hydroperoxide, which does not require a stage of heating the solution containing the water-soluble organic peroxide or of addition of salts or of base which can destabilize the organic peroxide.

SUMMARY OF THE INVENTION

The invention relates to a process for the concentration of a composition comprising at least one water-soluble organic peroxide, said process comprising a stage of bringing said composition into contact with a reverse osmosis membrane.

The present invention makes it possible to satisfy the need expressed above. It more particularly provides a process for the concentration of a composition comprising a water-soluble organic peroxide which is efficient and safer because it does not require heating of the organic peroxide or the addition of salts or of base which can reduce the stability of the organic peroxide.

It is known to use the reverse osmosis technique to concentrate hydrogen peroxide. However, the latter always generates only a single phase whatever its concentration in the water. On the contrary, it appears that, during their concentration, water-soluble organic peroxides, in particular organic hydroperoxides, in solution in water form two distinct phases (an organic phase and an aqueous phase) starting from a certain concentration of organic peroxide. Surprisingly, it has been discovered that the reverse osmosis technique makes possible the concentration of a water-soluble organic peroxide despite the appearance of this two-phase system in the immediate vicinity of the reverse osmosis membrane.

The invention is particularly useful for the reconcentration of dilute solutions of water-soluble organic peroxide, for example resulting from washing stages.

BRIEF DESCRIPTION OF THE FIGURE

FIG. 1 represents a diagrammatic view of an apparatus making possible the implementation of the process according to the invention.

DESCRIPTION OF EMBODIMENTS OF THE INVENTION

The invention is now described in greater detail and in a nonlimiting manner in the description which follows.

In the present description, unless expressly indicated otherwise, all the percentages (%) shown are percentages by weight.

Concentration of the Composition Comprising the Water-Soluble Organic Peroxide

In a first aspect, the invention relates to a process for the concentration of a composition comprising at least one water-soluble organic peroxide, said process comprising a stage of bringing said composition into contact with a reverse osmosis membrane.

This contacting stage makes it possible to obtain a retentate and a permeate, the water-soluble organic peroxide being concentrated in the retentate.

Within the meaning of the present invention, the term "a water-soluble organic peroxide" can mean one or more water-soluble organic peroxides. It is the same for the other entities mentioned in the present description.

Within the meaning of the present invention, the term "composition" is understood to mean the composition to be concentrated. Preferably, said composition is an aqueous composition.

The term "composition to be concentrated" is understood to mean the composition before bringing into contact with a reverse osmosis membrane.

Within the meaning of the present invention, the term "a water-soluble organic peroxide" is understood to mean an organic peroxide exhibiting a solubility in an aqueous solution, in particular in pure water, of greater than or equal to 1 g/l, preferably of greater than or equal to 10 g/l, preferably of greater than or equal to 30 g/l, more preferentially still of greater than or equal to 45 g/l, at the temperature at which the stage of bringing the composition into contact with the reverse osmosis membrane is carried out. Advantageously, said water-soluble organic peroxide has a solubility in an aqueous solution, in particular in pure water, of greater than or equal to 1 g/l, preferably of greater than or equal to 10 g/l, preferably of greater than or equal to 30 g/l, more preferentially still of greater than or equal to 45 g/l, at a temperature of 20 to 25° C.

In particular, the term "a water-soluble organic peroxide" is understood to mean an organic peroxide exhibiting a solubility in the aqueous composition to be concentrated according to the invention of greater than or equal to 1 g/l, preferably of greater than or equal to 10 g/l, preferably of greater than or equal to 30 g/l, more preferentially still of greater than or equal to 45 g/l, at the temperature at which the stage of bringing the composition into contact with the reverse osmosis membrane is carried out. Advantageously, said water-soluble organic peroxide has a solubility in the aqueous composition to be concentrated according to the invention of greater than or equal to 1 g/l, preferably of greater than or equal to 10 g/l, preferably of greater than or equal to 30 g/l, more preferentially still of greater than or equal to 45 g/l, at a temperature of 20 to 25° C.

The solubility can be measured by any technique known to a person skilled in the art, such as iodometry, chromatography or by the measurement of the total organic carbon (TOC).

Preferably, the solubility is measured by gas chromatography.

Reverse osmosis is a technique which makes it possible to concentrate an aqueous solution comprising one or more entities to be concentrated using a membrane making possible the passage of water but not of the entity or entities to be concentrated. The pressure exerted on the solution to be concentrated forces the water to pass through the membrane and, once the membrane has been crossed, constitutes the permeate while the entity or entities to be concentrated are retained by the membrane and thus represents the retentate. Consequently, said at least one water-soluble organic peroxide is concentrated in the retentate.

The term "the water-soluble organic peroxide being concentrated in the retentate" is understood to mean that the concentration by weight of the at least one water-soluble organic peroxide in the retentate is greater than that in the permeate. Furthermore, the concentration by weight of the water-soluble organic peroxide in the retentate is greater than that in the composition before concentration.

Preferably, the process according to the invention does not comprise the addition of salt and/or of base before the stage of bringing said composition into contact with a reverse osmosis membrane. In particular, the process does not comprise a stage of addition of salt and/or of base to the composition to be concentrated.

The reverse osmosis can be carried out using all suitable membranes, such as acetate, polyacrylonitrile, polysulfone, polyvinylidene fluoride or polyamide membranes, preferably polyamide membranes.

Advantageously, the composition to be concentrated has a pH of less than or equal to 8, preferably of less than or equal to 7.5, more preferentially of less than or equal to 7.

Preferably, the composition to be concentrated has a pH of greater than or equal to 5, more preferentially of greater than or equal to 6, preferentially again of greater than or equal to 6.5.

The reverse osmosis, that is to say the bringing of the composition into contact with the reverse osmosis membrane, can be carried out at a pressure of between 20 and 70 atmospheres, preferably between 25 and 60 atmospheres. In other words, the reverse osmosis can be carried out at a pressure of between 2026 kPa and 7092 kPa, preferentially between 2533 kPa and 6079 kPa, or between approximately 2000 kPa and approximately 7000 kPa, preferentially between approximately 2500 kPa and approximately 6000 kPa. Preferably, the pressure increases during the contacting stage, so as to keep the permeate flow rate constant. More preferentially still, the pressure increases during the progression of the reverse osmosis but remains within the ranges specified above.

The concentration by reverse osmosis, and thus in particular the stage of bringing said composition into contact with the reverse osmosis membrane, can be carried out at a temperature ranging from 0° C. to 60° C., preferably from 5° C. to 50° C., more preferentially from 10° C. to 45° C., more preferentially still from 15° C. to 30° C.

According to embodiments, the percentage by weight of water-soluble organic peroxide in the retentate is greater by at least 1.05 times, preferably by at least 1.1 times, preferably by at least 1.2 times, preferably by at least 1.3 times, preferably by at least 1.5 times, preferably by at least 2 times and more preferably by at least 3 times, with respect to the percentage by weight of water-soluble organic peroxide in the composition before concentration.

Particularly advantageously, the composition is concentrated by reverse osmosis at least until the appearance of two phases in the retentate. In this case, the retentate forms two immiscible phases consisting of a phase concentrated in water-soluble organic peroxide and of a dilute phase.

The terms "phase concentrated in water-soluble organic peroxide" and "phase diluted in water-soluble organic peroxide" are understood to mean that the concentration by weight of water-soluble organic peroxide in said phase concentrated in water-soluble organic peroxide is higher than that in the phase diluted in water-soluble organic peroxide. The phase concentrated in water-soluble organic peroxide corresponds to the organic phase and the phase diluted in water-soluble organic peroxide corresponds to the aqueous phase of this two-phase system.

Preferably, the percentage by weight of water-soluble organic peroxide in the phase concentrated in water-soluble organic peroxide is greater by at least 2 times, preferably by at least 3 times, preferably by at least 4 times, preferably by at least 5 times, preferably by at least 8 times, preferably by at least 10 times and more preferentially by at least 15 times, with respect to the percentage by weight of water-soluble organic peroxide in the composition before concentration.

Advantageously, all or part of the diluted phase is recycled with the composition comprising the water-soluble organic peroxide to be concentrated, before the stage of bringing into contact with a reverse osmosis membrane. In other words, all or part of the diluted phase is recovered and added to the composition comprising the water-soluble organic peroxide to be concentrated.

Advantageously, the water-soluble organic peroxide is an alkyl hydroperoxide.

The term "alkyl hydroperoxide" is understood to mean a compound of formula R—O—O—H in which R represents an alkyl group, which is linear or branched, cyclic or noncyclic, unsaturated or functionalized, or an aromatic group, which is optionally substituted, preferably having from 4 to 10 carbon atoms.

More particularly, R represents:
a linear or branched $C_4$-$C_{10}$, preferably $C_4$-$C_8$, more preferentially $C_4$-$C_6$, alkyl group optionally substituted by one or more hydroxyl groups, or a cyclic group comprising from 5 to 8 carbon atoms which is optionally aromatic and which is optionally substituted by one or more $C_1$-$C_3$ alkyl groups.

In particular, R can represent a cyclic group comprising from 5 to 8 carbon atoms which is optionally aromatic and which is optionally substituted by one or more $C_1$-$C_3$ alkyl groups, in particular by a $C_1$ alkyl group.

More particularly, R can represent a nonaromatic cyclic group comprising from 5 to 8 carbon atoms which is optionally substituted by a $C_1$ alkyl group.

Preferably, the alkyl hydroperoxide is a tert-alkyl hydroperoxide.

Preferably, $R^1$ represents a branched $C_4$-$C_{10}$, preferably $C_4$-$C_8$, more preferentially $C_4$-$C_6$, more preferentially still $C_4$-$C_5$, alkyl group.

Preferably, said alkyl hydroperoxide is chosen from the group consisting of tert-butyl hydroperoxide, tert-amyl hydroperoxide, hexylene glycol hydroperoxide, tert-octyl hydroperoxide, tert-hexyl hydroperoxide, methylcyclopentyl hydroperoxide and methylcyclohexyl hydroperoxide. Preferably, the water-soluble organic peroxide is chosen from the group consisting of tert-butyl hydroperoxide and tert-amyl hydroperoxide, more preferentially is tert-amyl hydroperoxide.

Preferably, the composition comprising the at least one water-soluble organic peroxide to be concentrated comprises from 1% to 50%, preferably from 1% to 20%, by weight of water-soluble organic peroxide, with respect to the total weight of the composition.

Particularly preferably, the composition comprising the at least one water-soluble organic peroxide to be concentrated is an aqueous solution, comprising preferably from 50% to 99% by weight of water, more preferentially from 80% to 99% of water, with respect to the total weight of the composition.

Separation of a Water-Soluble Organic Peroxide and of an Organic Dialkyl Peroxide According to another aspect, the invention relates to a process for the separation of at least one water-soluble organic peroxide and of at least one water-insoluble compound, comprising the following stages:

a) extraction, with an aqueous composition, of said at least one water-soluble organic peroxide from a composition comprising said at least one water-soluble organic peroxide and said at least one water-insoluble compound;

b) separation of the aqueous phase enriched in water-soluble organic peroxide and of the organic phase which are obtained in stage a);

c) concentration of said aqueous phase enriched in water-soluble organic peroxide according to the concentration process as described above.

It should be understood that the aqueous phase subjected to the concentration stage c) is equivalent to the composition comprising the water-soluble organic peroxide in the "Concentration of the composition comprising the water-soluble organic peroxide" section above. In particular, all the characteristics of the composition comprising the at least one water-soluble organic peroxide described above in connection with the concentration process can be applied to the aqueous phase subjected to the concentration stage c) in the separation process. Likewise, all the characteristics of the concentration process which are described above can be applied to the concentration stage c) of the separation process.

In particular, said composition comprising at least one water-soluble organic peroxide and at least one water-insoluble compound can be obtained during the synthesis of said at least one water-soluble organic peroxide. In this case, the composition obtained can comprise the water-soluble organic peroxide synthesized as well as one or more water-insoluble compounds, preferably one or more water-insoluble organic peroxides, more preferentially one or more dialkyl peroxides, as impurity formed during the synthesis of the water-soluble organic peroxide.

Within the meaning of the present invention, the term "a water-insoluble compound" or "a water-insoluble organic peroxide" is understood to mean a compound or an organic peroxide exhibiting a solubility in an aqueous solution, in particular in pure water, of less than 1 g/l, preferably of less than or equal to 0.8 g/l, preferably of less than or equal to 0.5 g/l, more preferentially still of less than or equal to 0.1 g/l, at the temperature at which the stage of bringing the composition into contact with the reverse osmosis membrane is carried out. More preferably, said water-insoluble compound or said water-insoluble organic peroxide is not miscible at all in water at the temperature at which the stage of bringing the composition into contact with the reverse osmosis membrane is carried out. Advantageously, said water-insoluble compound or said water-insoluble organic peroxide has a solubility in an aqueous solution, in particular in pure water, of less than 1 g/l, preferably of less than or equal to 0.8 g/l, preferably of less than or equal to 0.5 g/l, more preferentially still of less than or equal to 0.1 g/l, and more preferentially still is not miscible at all at a temperature of 20 to 25° C.

In particular, the term "a water-insoluble compound" or "a water-insoluble organic peroxide" is understood to mean a compound or an organic peroxide exhibiting a solubility in the aqueous phase enriched in water-soluble organic peroxide obtained after stage a) of less than 1 g/l, preferably of less than or equal to 0.8 g/l, preferably of less than or equal to 0.5 g/l, more preferentially still of less than or equal to 0.1 g/l, at the temperature at which the stage of bringing the composition into contact with the reverse osmosis membrane is carried out. More preferably, said water-insoluble compound or said water-insoluble organic peroxide is not miscible at all in the aqueous phase enriched in water-soluble organic peroxide obtained after stage a) at the temperature at which the stage of bringing the composition into contact with the reverse osmosis membrane is carried out. Advantageously, said water-insoluble compound or said water-insoluble organic peroxide has a solubility in the aqueous phase enriched in water-soluble organic peroxide obtained after stage a) of less than 1 g/l, preferably of less than or equal to 0.8 g/l, preferably of less than or equal to 0.5 g/l, more preferentially still of less than or equal to 0.1 g/l, and more preferentially still is not miscible at all at a temperature of 20 to 25° C.

The separation process according to the invention can comprise a stage a'), prior to stage a), of synthesis of said at least one water-soluble organic peroxide.

Stage a') of synthesis of the water-soluble organic peroxide can be carried out by any method known to a person skilled in the art resulting in the formation of water-insoluble compounds, in particular water-insoluble organic peroxides, as impurity. In particular, stage a') can be carried out by the reaction of at least one alcohol or at least one alkene with hydrogen peroxide in the presence of an acid, preferably sulfuric acid. Such a process leads in particular to the synthesis of dialkyl peroxide as impurities.

Preferably, the water-soluble organic peroxide can be prepared in an acidic medium.

In this case, the method for the preparation of the water-soluble organic peroxide consists in particular in reacting aqueous hydrogen peroxide solution in the presence of at least one alcohol or of at least one alkene in an acidic medium.

Preferably, the method for the preparation of the water-soluble organic peroxide consists in particular in reacting aqueous hydrogen peroxide solution in the presence of at least one alcohol or one unsaturated compound in an acidic medium.

The reaction can be carried out at a temperature which can range from 10° C. to 80° C., preferably 20° C. to 40° C.

Preferably, the reaction is carried out in the presence of one or more inorganic or organic acids, in particular one or more inorganic acids.

More preferentially, the inorganic acid is sulfuric acid.

The composition comprising at least one water-soluble organic peroxide and at least one water-insoluble compound (before stage a)) can comprise at least 50% by weight of water-soluble organic peroxide, preferably at least 60% by weight of water-soluble organic peroxide, more preferentially at least 68% by weight of water-soluble organic peroxide, more preferentially still at least 70% by weight of water-soluble organic peroxide, with respect to the total weight of organic peroxides.

According to embodiments, the composition comprising a water-soluble organic peroxide and a water-insoluble compound (before stage a)) comprises from 0.1% to 40% by weight of water-insoluble compound, preferably from 1% to 30% by weight of water-insoluble compound, more preferentially from 2% to 22% by weight of water-insoluble compound, more preferentially still from 3% to 20% by weight of water-insoluble compound, with respect to the total weight of water-soluble organic peroxides and water-insoluble compounds.

Preferably, said at least one water-insoluble compound is a water-insoluble organic peroxide, more preferentially is a dialkyl peroxide.

The term "dialkyl peroxide" is understood to mean a compound of formula $R_1$—O—O—$R_2$ in which $R_1$ and $R_2$ are identical or different and independently represent an alkyl group which is linear or branched, cyclic or noncyclic, unsaturated or functionalized, or an aromatic group, which is optionally substituted, preferably having from 4 to 10 carbon atoms.

Advantageously, $R^1$ and $R^2$, which are identical or different, in particular identical, represent:
- a linear or branched $C_4$-$C_{10}$, preferably $C_4$-$C_8$, more preferentially $C_4$-$C_6$, alkyl group optionally substituted by one or more hydroxide groups, or
- a cyclic group comprising from 5 to 8 carbon atoms which is optionally aromatic and which is optionally substituted by one or more $C_1$-$C_3$, in particular $C_1$, alkyl groups.

In particular, $R^1$ and $R^2$ can represent a cyclic group comprising from 5 to 8 carbon atoms which is optionally aromatic and which is optionally substituted by one or more $C_1$-$C_3$, in particular $C_1$, alkyl groups.

More particularly, $R^1$ and $R^2$ can represent a nonaromatic cyclic group comprising from 5 to 8 carbon atoms which is optionally substituted by a $C_1$ alkyl group.

Preferably, the dialkyl peroxide is a di(tert-alkyl) peroxide.

Preferably, $R^1$ and $R^2$, which are identical or different, represent a branched $C_4$-$C_{10}$, preferably $C_4$-$C_8$, more preferentially $C_4$-$C_6$, alkyl group optionally substituted by one or more hydroxide groups.

Preferably, $R^1$ and $R^2$, which are identical or different, represent a branched $C_4$-$C_{10}$, preferably $C_4$-$C_8$, more preferentially $C_4$-$C_6$, alkyl group.

More preferentially still, the dialkyl peroxide is symmetrical, that is to say that the groups flanking the 0-0 group are identical. In other words, $R^1$ and $R^2$ are more preferentially identical and represent a branched $C_4$-$C_{10}$, preferably $C_4$-$C_8$, more preferentially $C_4$-$C_6$, alkyl group.

Mention may be made, as dialkyl peroxide to be separated from the hydroperoxide, of di(tert-butyl) peroxide, di(tert-amyl) peroxide, di(3-hydroxy-1,1-dimethylbutyl) peroxide, di(tert-octyl) peroxide, di(tert-hexyl) peroxide, di(methylcyclopentyl) peroxide or di(methylcyclohexyl) peroxide. In particular, the dialkyl peroxide is symmetrical, that is to say that the groups flanking the O—O group are identical.

More preferentially, the dialkyl peroxide is chosen from the group consisting of di (tert-butyl) and di(tert-amyl) peroxide.

More preferentially still, the dialkyl peroxide is di(tert-amyl) peroxide.

Advantageously, the alkyl hydroperoxide and the dialkyl peroxide have identical R, $R^1$ and $R^2$ groups.

The characteristics of the water-soluble organic peroxide which are described in connection with the above concentration process can be applied in the same way to the water-soluble organic peroxide in the context of the separation process.

Advantageously, said at least one water-soluble organic peroxide, preferably said at least one hydroperoxide, and said at least one dialkyl peroxide exhibit identical R, $R_1$ and $R_2$ groups.

For example, the water-soluble organic peroxide is tert-butyl hydroperoxide and the dialkyl peroxide is di(tert-butyl) peroxide.

Alternatively, the water-soluble organic peroxide is tert-amyl hydroperoxide and the dialkyl peroxide is di(tert-amyl) peroxide.

Alternatively, the water-soluble organic peroxide is hexylene glycol hydroperoxide and the dialkyl peroxide is di(3-hydroxy-1,1-dimethylbutyl) peroxide.

Alternatively, the water-soluble organic peroxide is tert-octyl hydroperoxide and the dialkyl peroxide is di(tert-octyl) peroxide.

Alternatively, the water-soluble organic peroxide is tert-hexyl hydroperoxide and the dialkyl peroxide is di(tert-hexyl) peroxide.

The process according to the invention comprises a stage a) of extraction, with an aqueous composition, of said at least one water-soluble organic peroxide. This stage makes it possible to obtain an aqueous phase enriched in water-soluble organic peroxide and an organic phase.

The term "extraction with an aqueous composition" is understood to mean the addition of an aqueous composition to the composition comprising said at least one water-soluble organic peroxide and said at least one water-insoluble compound, optionally followed by the mixing of the aqueous composition with the composition comprising said water-soluble organic peroxide and said water-insoluble compound, so that the water-soluble organic peroxide is at least partly transferred into the aqueous phase. The water-insoluble compound is not or is poorly soluble in water and most of this compound is not transferred into the aqueous phase and remains in the organic phase.

Advantageously, the aqueous composition used for the extraction, or in other words added in stage a), comprises at least 50% by weight of water, preferably at least 70% by weight of water, more preferentially at least 90% by weight of water, more preferentially still at least 95% by weight of water, more preferentially still at least 97% by weight of water and more preferentially still at least 99% by weight of water, with respect to the total weight of the composition. According to preferred embodiments, the aqueous composition is water.

Preferably, the aqueous composition used for the extraction, or in other words added in stage a), has a pH of less than or equal to 8, preferably of less than or equal to 7.5, more preferentially of less than or equal to 7.

Preferably, the aqueous composition used for the extraction, or in other words added in stage a), preferably has a pH of greater than or equal to 5, more preferentially of greater than or equal to 6, more preferentially of greater than or equal to 6.5.

Preferably, the salt content of the aqueous composition used for the extraction, or in other words added in stage a), is less than or equal to 10 g/l, preferably less than or equal to 5 g/l, preferably less than or equal to 1 g/l, preferably less than or equal to 0.5 g/l. Preferably, the aqueous composition is devoid of salt and/or of ionized entity and/or of base and/or of acid.

Preferably, the aqueous composition used for the extraction, or in other words added in stage a), is devoid of salt, such as sodium chloride, potassium chloride or sulfates. This exhibits the advantage of limiting the presence of ions in the aqueous phase, after extraction with said aqueous composition, which would increase the osmotic pressure of the aqueous phase and might destabilize the water-soluble organic peroxide.

The term "aqueous phase enriched in water-soluble organic peroxide" is understood to mean that the ratio of the concentration by weight of said at least one water-soluble organic peroxide to the concentration by weight of said at least one water-insoluble compound in the aqueous phase is greater than that of the composition comprising said at least one water-soluble organic peroxide and said at least one water-insoluble compound before stage a).

The molar concentrations and/or the percentages by weight of the water-soluble organic peroxide and of the water-insoluble compound can be determined by iodometry, chromatography or by measurement of the total organic carbon (TOC).

The extraction stage a) can be carried out at a temperature ranging from 0° C. to 60° C., preferably from 5° C. to 50° C., more preferentially from 10° C. to 45° C., more preferentially still from 15° C. to 30° C.

Stage b) of separation of the aqueous phase and of the organic phase makes it possible to separate the aqueous phase comprising most of the water-soluble organic peroxide from the organic phase comprising most of the water-insoluble compound, preferably water-insoluble peroxide, more preferentially dialkyl peroxide.

This stage b) can be carried out by any means known to a person skilled in the art. In particular, stage b) can be carried out by separation by settling, by centrifugation or by coalescence. The separation of stage b) can, for example, be carried out using a decanter, a centrifuge or a coalescer.

The process according to the invention also comprises a stage c) of concentration of said aqueous phase according to the concentration process as described above.

Preferably, the process according to the invention does not comprise the addition of salt and/or of base before stage c) of concentration of the aqueous phase. In particular, the process does not comprise a stage of addition of salt and/or of base to the aqueous phase.

All or part of the permeate obtained in stage c) can be recycled with the aqueous composition, in stage a).

Preferably, the percentage by weight of water-insoluble compound, preferably of water-insoluble organic peroxide, preferably dialkyl peroxide, in the retentate obtained in stage c) is reduced, with respect to that in the composition comprising said at least one water-soluble organic peroxide and said at least one water-insoluble compound before stage a), by at least 50%, preferably by at least 60%, preferably by at least 68%, or by at least 70%, or by at least 80%, or by at least 90%, or by at least 95%, or by at least 97%, or by at least 99%, or by at least 99.5%, or by at least 99.9%, or by at least 99.95%.

Composition

The invention also relates to an aqueous composition containing at least 60% by weight of alkyl hydroperoxide as defined above and less than 0.1% by weight of dialkyl peroxide as defined above, the proportions being calculated by weight, with respect to the total weight of the composition.

Preferably, the aqueous composition contains at least 68% by weight of alkyl hydroperoxide as defined above, preferably at least 70% and more preferentially at least 80% by weight.

Preferably, $R_1$ represents a branched $C_4$-$C_{10}$, preferably $C_5$-$C_{10}$, preferably $C_5$-$C_8$, more preferentially $C_5$-$C_6$, more preferentially still $C_5$, alkyl group which is optionally substituted.

The alkyl hydroperoxide is preferably chosen from the group consisting of tert-amyl hydroperoxide, hexylene glycol hydroperoxide, tert-octyl hydroperoxide and tert-hexyl hydroperoxide.

More preferentially, the alkyl hydroperoxide is tert-amyl hydroperoxide (TAHP).

Advantageously, the aqueous composition contains less than 0.08% by weight, preferably less than 0.07% by weight, of dialkyl peroxide, preferably less than 0.05% by weight of dialkyl peroxide, preferably less than 0.025% by weight of dialkyl peroxide, more preferentially less than 0.01% by weight of dialkyl peroxide, with respect to the total weight of the composition.

Preferably, the dialkyl peroxide is chosen from the group consisting of di(tert-amyl) peroxide, di(3-hydroxy-1,1-dimethylbutyl) peroxide, di(tert-octyl) peroxide and di(tert-hexyl) peroxide.

More preferentially, the dialkyl peroxide is di(tert-amyl) peroxide.

Advantageously, the aqueous composition contains at least 68% by weight of tert-amyl hydroperoxide (TAHP) and less than 0.1% by weight of di(tert-amyl) peroxide (DTA), the proportions being calculated by weight with respect to the total weight of the composition.

The present invention also relates to an aqueous composition rich in alkyl hydroperoxide capable of being obtained by the process according to the invention.

Use of the Composition

The present invention also relates to the use of the composition as defined above for the preparation of cross-linking agent(s) or of polymerization initiator(s).

Preferably, the initiator(s) is or are initiators of polymerization by the radical route, in particular of ethylene under high pressure.

The term "high pressure" is understood to mean, within the meaning of the present invention, a pressure of greater than 50 MPa. Preferably, the pressure varies from 500 bar (50 MPa) to 3000 bar (300 MPa), preferentially from 1200 bar (120 MPa) to 3000 bar (300 MPa), better still from 1200 bar (120 MPa) to 2600 bar (260 MPa).

Preferably, the crosslinking agents or the polymerization initiators are chosen from the group consisting of organic peroxides, in particular peroxyesters, hemiperoxyacetals and peroxyacetals.

The term "hemiperoxyacetal" is understood to mean a compound of general formula $(R_3)(R_4)C(—OR_1)(—OOR_2)$ in which:

$R_1$ represents a linear or branched, preferably $C_1$-$C_{12}$, preferably $C_1$-$C_4$, more preferably $C_1$, alkyl group or a cycloalkyl group with $R_2$, $R_2$ represents a linear or branched, preferably $C_1$-$C_{12}$, preferably $C_4$-$C_{12}$, more preferably $C_5$, alkyl group or a cycloalkyl group with $R_1$, $R_3$ represents a hydrogen or a linear or branched, preferably $C_1$-$C_{12}$, more preferably $C_4$-$C_{12}$, alkyl group or a cycloalkyl group with $R_4$, $R_4$ represents a hydrogen or a linear or branched, preferably $C_1$-$C_{12}$, more preferably $C_4$-$C_{12}$, alkyl group or a cycloalkyl group with $R_3$.

Preferably, $R_3$ forms a cycloalkyl group with $R_4$.

Preferably, when $R_3$ is a hydrogen, $R_4$ is a linear or branched, preferably $C_1$-$C_{12}$, more preferably $C_4$-$C_{12}$, alkyl group.

EXAMPLES

The following examples illustrate the invention without limiting it.

A hydroperoxide is first brought into contact with demineralized water in a batch reactor. When two phases appear in the reactor, they are separated by settling in order to obtain clear solutions. The aqueous phase recovered, containing the hydroperoxide, is subsequently reconcentrated by reverse osmosis. This stage is carried out in an apparatus such as represented in FIG. 1.

The product to be treated is stored in a stirred and temperature-controlled container (1). It is subsequently fed into the membrane module (3) by a high pressure pump (2). The permeate separated by the membrane is collected via the outlet (4) of the module (3) and the retentate produced is recycled to the container (1). The pressure regulator (5) makes it possible to control and to pressurize the installation. The heat exchanger (6) makes it possible to maintain the temperature of the liquid returning to the container (1).

The membranes used are commercial polyamide-type membranes. The membrane surface areas used in the tests are 140 cm² and 2.6 m².

The analyses are carried out by gas chromatography in the various streams (on a GC column: J&W DB-1 (15 meters× 0.530 μm-1.50 μm of phase, Carrier gas: helium at 3 ml/min, Injector temperature: 90° C., Detector temperature: 250° C., Temperature gradient: 60° C. for 4 min, then 15° C./min up to 140° C. (no stationary phase), then 30° C./min up to 220° C., then stationary phase of 2 min. Injection: 2 μl).

Example 1

2503 g of aqueous phase containing 14.6% by weight of TBHP are fed into the membrane module, equipped with a Dow Filmtec™ SW30 polyamide membrane (surface area: 140 cm², circulation flow rate of 480 l/h provided by the high pressure pump (2)). The temperature of the aqueous phase is kept constant at 26° C. A pressure increasing from 47 to 53 atmospheres (i.e., approximately 4762 to 5370 kPa) is applied.

The following results are obtained over time.

TABLE 1

| Time (min) | Pressure (atm) | Cumulative permeate weight (g) | TBHP in the permeate (% by weight) | Permeate flux (kg/h · m²) |
|---|---|---|---|---|
| 30 | 47 | 70.1 | 1.0 | 9.9 |
| 60 | 49 | 140.7 | 0.9 | 10.2 |
| 120 | 51 | 285.3 | 0.8 | 10.4 |
| 150 | 51 | 360.7 | 0.8 | 10.4 |
| 180 | 51 | 433.2 | 0.8 | 9.6 |
| 210 | 53 | 513.2 | 0.7 | 10.8 |
| 240 | 53 | 591.4 | 0.7 | 10.9 |
| 260 | 53 | 644.4 | 0.7 | 10.9 |

At the end of the test, 1.86 kg of retentate are recovered. After separation by settling, the following are recovered:

178 g of organic phase (phase concentrated in hydroperoxide) containing 70% by weight of TBHP, water: qsp;
1680 g of aqueous phase (diluted phase) with the composition: TBHP: 14% by weight, water: qsp.

Example 2

201.6 g of a tert-amyl hydroperoxide (TAHP) solution having the following composition: TAHP: 85% by weight, di(tert-amyl) peroxide (DTAP): 5% by weight, water: qsp, are mixed with 2399 g of water. After separation by settling, 95.5 g of organic phase, predominantly composed of DTAP, and 2505 g of an aqueous phase containing 4.5% by weight of TAHP are obtained. This aqueous phase is fed into the membrane module, equipped with a GE-Suez Water type AD polyamide membrane (surface area of the membrane: 140 cm², circulation flow rate of 480 l/h). The temperature of the aqueous phase is maintained at 25° C.-26° C. A pressure increasing from 40 to 47 atmospheres (i.e., approximately 4053 to 4762 kPa) is applied to the membrane.

The following results are obtained over time.

TABLE 2

| Time (min) | Pressure (atm) | Cumulative permeate weight (g) | TAHP in the permeate (% by weight) | Permeate flux (kg/h · m²) |
|---|---|---|---|---|
| 30 | 40 | 56.8 | 0.3 | 7.8 |
| 60 | 40 | 108.5 | 0.3 | 7.2 |
| 120 | 43 | 214.4 | 0.3 | 7.5 |
| 180 | 44 | 319.2 | 0.2 | 7.3 |
| 240 | 45 | 421.9 | 0.2 | 7.3 |
| 300 | 46 | 528.7 | 0.2 | 7.4 |
| 360 | 47 | 631.8 | 0.2 | 7.2 |

At the end of the test, 1.873 kg of retentate are recovered. After separation by settling, the following are recovered:

23 g of organic phase (phase concentrated in hydroperoxide) with the composition: TAHP: 85% by weight, DTAP: less than 200 ppm by weight, water: qsp;
1850 g of aqueous phase (diluted phase) with the composition TAHP: 4.5% by weight, water: qsp.

Example 3

3.7 kg of a tert-amyl hydroperoxide solution having the following composition: TAHP: 85% by weight, DTAP: 5% by weight, water: qsp, are mixed with 48 kg of water. After separation of the organic phase predominantly composed of DTAP, 46.3 kg of an aqueous phase containing 4.8% by weight of TAHP are obtained. This solution is fed into a membrane module, equipped with a Dow Filmtec™ SW30 polyamide membrane (surface area of the membrane: 2.6 m², circulation flow rate of 480 l/h). The temperature of the aqueous phase is maintained at 25° C. A pressure increasing from 40 to 50 atm (i.e., approximately 4053 kPa to 5066 kPa) is applied to the membrane.

The following results are obtained over time.

TABLE 3

| Time (min) | Pressure (atm) | Cumulative permeate weight (kg) | TAHP in the permeate (% by weight) | Permeate flux (kg/h · m²) |
|---|---|---|---|---|
| 30 | 40 | 10.4 | 0.1 | 6.3 |
| 60 | 50 | 18.0 | 0.1 | 6.1 |
| 90 | 50 | 25.1 | 0.2 | 5.1 |
| 120 | 50 | 31.3 | 0.2 | 4.0 |
| 135 | 50 | 34.4 | 0.2 | 4.4 |

At the end of the test, 11.9 kg of retentate are recovered. After separation by settling, the following are recovered:
1980 g of organic phase (phase concentrated in hydroperoxide) with the composition: TAHP: 85% by weight, DTAP: less than 200 ppm by weight, water: qsp;
9920 g of aqueous phase (diluted phase) with the composition: TAHP: 4.8% by weight, water: qsp.

Example 4

In a batch reactor, 1577 g of water are mixed with 1155 g of DTBP (99% by weight) and 515 g of a tert-butyl hydroperoxide solution (68% by weight, water: qsp). After separation by settling, 1388 g of organic phase composed predominantly of DTBP and 1854 g of aqueous phase containing 6.7% by weight of TBHP are obtained. This solution is fed into a membrane module, equipped with a Dow Filmtec™ SW30 polyamide membrane (surface area: 140 cm², circulation flow rate of 480 l/h provided by the high pressure pump (2)). The temperature of the aqueous phase is maintained at 25° C. A pressure increasing from 40 to 50 atmospheres (i.e., approximately 4053 kPa to 5066 kPa) is applied to the membrane.

The following results are obtained over time.

TABLE 4

| Time (min) | Pressure (atm) | Cumulative permeate weight (g) | TBHP in the permeate (% by weight) | Permeate flux (kg/h · m²) |
|---|---|---|---|---|
| 30 | 40 | 76.3 | 0.5 | 10.9 |
| 180 | 45 | 470.4 | 0.3 | 11.2 |
| 360 | 50 | 949.2 | 0.3 | 11.3 |
| 605 | 50 | 1609.3 | 0.3 | 11.4 |

At the end of the test, 245 g of retentate are recovered. After separation by settling, the following are recovered:
148 g of organic phase (phase concentrated in hydroperoxide) containing 70% by weight of TBHP, 500 ppm by weight of Dl; water: qsp;
97 g of aqueous phase (diluted phase) with the composition: TBHP: 16% by weight, water: qsp.

The invention claimed is:

1. A process for the concentration of a composition comprising at least one water-soluble organic peroxide, wherein the composition has a pH of less than or equal to 8 and greater than or equal to 5, said process comprising a stage of bringing said composition into contact with a reverse osmosis membrane.

2. The process as claimed in claim 1, in which the stage of bringing said composition into contact with the reverse osmosis membrane is carried out at a temperature ranging from 0° C. to 60° C.

3. The process as claimed in claim 1, in which the stage of bringing into contact is carried out at a pressure of between approximately 2000 and approximately 7000 kPa.

4. The process as claimed in claim 1, for obtaining a retentate forming two immiscible phases consisting of a phase concentrated in water-soluble organic peroxide and a phase diluted in water-soluble organic peroxide.

5. The process as claimed in claim 1, in which said at least one water-soluble organic peroxide is an alkyl hydroperoxide.

6. A process for the concentration of a composition comprising at least one water-soluble organic peroxide, said process comprising a stage of bringing said composition into contact with a reverse osmosis membrane, for obtaining a retentate forming two immiscible phases consisting of a phase concentrated in water-soluble organic peroxide and a phase diluted in water-soluble organic peroxide, in which all or part of the diluted phase is recycled with the composition comprising the water-soluble organic peroxide to be concentrated.

7. A process for the separation of at least one water-soluble organic peroxide and of at least one water-insoluble compound, comprising the following stages:
a) extraction, with an aqueous composition, of said water-soluble organic peroxide from a composition comprising said at least one water-soluble organic peroxide and said at least one water-insoluble compound, wherein an aqueous phase enriched in water-soluble organic peroxide and an organic phase are obtained;
b) separation of the aqueous phase enriched in water-soluble organic peroxide and of the organic phase which are obtained in stage a);
c) concentration of said aqueous phase enriched in water-soluble organic peroxide by a concentration process comprising bringing said aqueous phase enriched in water-soluble organic peroxide into contact with a reverse osmosis membrane.

8. The process as claimed in claim 7, not comprising the addition of salt or of base before stage c) of concentration of the aqueous phase.

9. The process as claimed in claim 7, in which the aqueous phase as defined in claim 7 has a pH of less than or equal to 8 and greater than or equal to 5.

10. The process as claimed in claim 7, in which stage b) is carried out by separation by settling, centrifugation or coalescence.

11. The process as claimed in claim 7, comprising a stage a'), prior to stage a), of synthesis of said at least one water-soluble organic peroxide.

12. The process as claimed in claim 7, in which stage a') is carried out by the reaction of at least one alcohol or at least one alkene with hydrogen peroxide in the presence of an acid.

13. The process as claimed in claim 7, in which said at least one water-soluble organic peroxide is tert-butyl hydroperoxide and said at least one water-insoluble compound is di(tert-butyl) peroxide.

14. The process as claimed in claim 7, in which said at least one water-soluble organic peroxide is tert-amyl hydroperoxide and said at least one water-insoluble compound is di(tert-amyl) peroxide.

* * * * *